(12) United States Patent
Flaherty et al.

(10) Patent No.: US 8,257,651 B2
(45) Date of Patent: Sep. 4, 2012

(54) ANALYTE METER WITH ROTATABLE USER INTERFACE

(75) Inventors: Joseph Flaherty, Westford, MA (US); Timothy Golnik, Boxford, MA (US)

(73) Assignee: AgaMatrix, Inc., Salem, NH (US)

( * ) Notice: Subject to any disclaimer, the term of this patent is extended or adjusted under 35 U.S.C. 154(b) by 1565 days.

(21) Appl. No.: 11/276,841

(22) Filed: Mar. 16, 2006

(65) Prior Publication Data
US 2007/0218543 A1   Sep. 20, 2007

(51) Int. Cl.
*G01N 15/06* (2006.01)
(52) U.S. Cl. ........ 422/68.1; 422/52; 422/73; 422/82.01; 422/82.02; 422/82.05; 422/82.08; 422/82.09; 422/82.11; 422/400; 422/407; 422/420; 422/421; 422/425; 422/430; 422/501; 422/502; 422/503; 422/504; 436/164; 436/177; 436/43; 436/63; 436/172; 436/149; 436/174; 436/518; 436/805; 436/809; 435/29; 435/4; 435/287.1; 435/7.1; 435/285.2; 506/30; 250/214.1; 250/251; 250/576; 530/408; 714/752
(58) Field of Classification Search .................... 422/58, 422/52, 73, 68.1, 82.01, 82.02, 82.05, 82.08, 422/82.09, 82.11, 99, 102, 400, 407, 420, 422/421, 425, 430, 501, 502, 503, 504; 435/287.1, 435/29, 4, 6, 7.1, 285.2; 436/164, 177, 43, 436/63, 149, 172, 174, 518, 805, 809; 506/30; 250/214.1, 251, 576; 530/408; 714/752

See application file for complete search history.

(56) References Cited

U.S. PATENT DOCUMENTS

| | | | |
|---|---|---|---|
| 5,728,074 A | | 3/1998 | Castellano et al. |
| 5,925,021 A | * | 7/1999 | Castellano et al. ........... 604/207 |
| 6,525,330 B2 | | 2/2003 | Paolini et al. |
| 6,585,698 B1 | | 7/2003 | Packman et al. |
| 2002/0085952 A1 | * | 7/2002 | Ellingboe et al. ................ 422/45 |
| 2002/0193679 A1 | | 12/2002 | Malave et al. |
| 2005/0258035 A1 | | 11/2005 | Harding et al. |
| 2005/0265094 A1 | | 12/2005 | Harding et al. |

* cited by examiner

*Primary Examiner* — Dennis M White
(74) *Attorney, Agent, or Firm* — Larson & Anderson, LLC (57) ABSTRACT

In one embodiment the present invention provides a blood analyte meter that is user-friendly and easy to use. In accordance with an embodiment of the present invention an analyte measurement device, for use with a test strip for determining the amount of an analyte in a sample, displays a hierarchy of information or options to a user. The hierarchy of information or options may include, among other information or options, subroutines that are performable by the processor of the device, stored data related to past tests performed by the user, and alarm features of the device. A user scrolls through and selects individual options or pieces of information by rotating and translating a rotatable user interface around and along an axis of rotation.

25 Claims, 9 Drawing Sheets

ANALYTE METER WITH ROTATABLE USER INTERFACE

BACKGROUND

Analyte meters are typically used for the measurement of an analyte in a sample. More particularly they are often used for the detection of the concentration of glucose within blood. For example, a diabetic may be required to use a glucose meter several times a day times a day in order to monitor the glucose levels within their blood. The diabetic user is often required to carry the meter, a lancet device for effecting a wound large enough to sample blood from, as well as diagnostic test strips on their person as they perform their daily routines to ensure that they can perform a blood glucose measurement at any given time. In order to facilitate the ease of carrying these items it is desirable to make them small, so that they can fit in an enclosure that is easily maneuverable (such as a purse). Further the devices should be user-friendly and easy to use.

SUMMARY OF INVENTION

An analyte measurement device, for use with a test strip for determining the amount of an analyte in a sample is provided. The device comprises (1) an analyte meter, (2) a housing, and (3) a rotatable user interface.

The analyte meter of the device comprises: (i) a processor programmed to display a hierarchy of information or options having a plurality of levels; (ii) a test strip interface for receiving a diagnostic test strip; and (iii) a meter display communicatively coupled to the processor for displaying the hierarchy of information or options to a user. Each level of the plurality of levels comprises information or options selected from the group consisting of: a selectable lower level, a selectable upper level, a selectable subroutine performable by the processor, and a selectable parameter. One of the plurality of levels includes a selectable subroutine performable by the processor that is a diagnostic test subroutine where the processor is programmed to perform a diagnostic test on a sample applied to a test strip received within the test strip interface to determine a concentration of an analyte within the sample, and to store data in the hierarchy of information related to the test.

The housing of the device has the meter disposed therein and has a display opening sized to receive the meter display and to make it externally visible to a user. The housing also has a test strip opening sized to receive a test strip.

The rotatable user interface of the device is communicatively coupled to the processor and accessible on the outside of the housing. The rotatable user interface is also rotationally and translationally connected about the housing to permit rotation around an axis of rotation and translation along the axis of rotation. When the rotatable user interface is: (i) rotated around the axis of rotation, the meter display scrolls through information in an open level of information of the plurality of levels of information; and (ii) translationally moved along the axis of rotation, a lower level of information is selected, an upper level of information is selected, a subroutine is selected, or a parameter is selected from the open level of information.

DETAILED DESCRIPTION OF THE INVENTION

It is often an advantage in the analyte detection industry to provide diagnostic meters that are as small as possible to allow a user to carry them with the utmost ease. However, a user of such a meter may be arthritic or have some other physical impairment which would hinder their ability to manipulate the function keys or other user interfaces of the smaller meters. As a result, many patients may not be able to, or simply decide not to sample blood as frequently as suggested by their doctors in order to monitor their physiological functions adequately. The present invention solves these problems and provides an improved analyte measurement device that is user-friendly and easy to use.

In the specification and the claims which follow, reference will be made to a number of terms which shall be defined to have the following meanings:

The term "hierarchy of information or options" is herein understood to mean a meter operation hierarchy comprising a plurality of levels that contain individual selections which allow a user to select and/or review: information, options, parameters, subroutines, levels within the hierarchy, and any combination thereof.

A "rotatable user interface" is herein understood to mean a user interface, that is accessible on the outside of the device housing, that when rotated about its axis of rotation, the meter display will scroll through an open level in the hierarchy of information or options.

The term "test strip opening" as it is used with regard to the device housing is herein understood to mean that the device allows for a disposable test strip to be inserted and removed from the test strip interface of analyte meter disposed within the housing. In one embodiment the "test strip opening" is large enough to receive a test strip within the housing such that the test strip interface of the meter is protected by the housing.

A "meter display" is herein understood to mean a display that provides information or options contained in the hierarchy to a user. The "meter display" is not particularly limited and may be, for example, a liquid-crystal display.

In accordance with an embodiment of the present invention an analyte measurement device, having a housing and a processor programmed to display a hierarchy of information or options having a plurality of levels to a user and programmed to perform, and store data related to, a diagnostic test on a sample to determine a concentration of an analyte within the sample, has the improvement comprising: a rotatable user interface communicatively coupled to the processor and accessible on the outside of the housing, wherein the user interface is rotationally and translationally connected about the housing to permit rotation around an axis of rotation generally parallel to the central axis of the housing and translation along the axis of rotation, wherein when the rotatable user interface is:
  (i) rotated around the axis of rotation, the meter display scrolls through information or options in an open level, and
  (ii) translationally moved along the axis of rotation, a lower level is selected, an upper level is selected, a subroutine is selected, or a parameter is selected from the open level.

Figure 1:
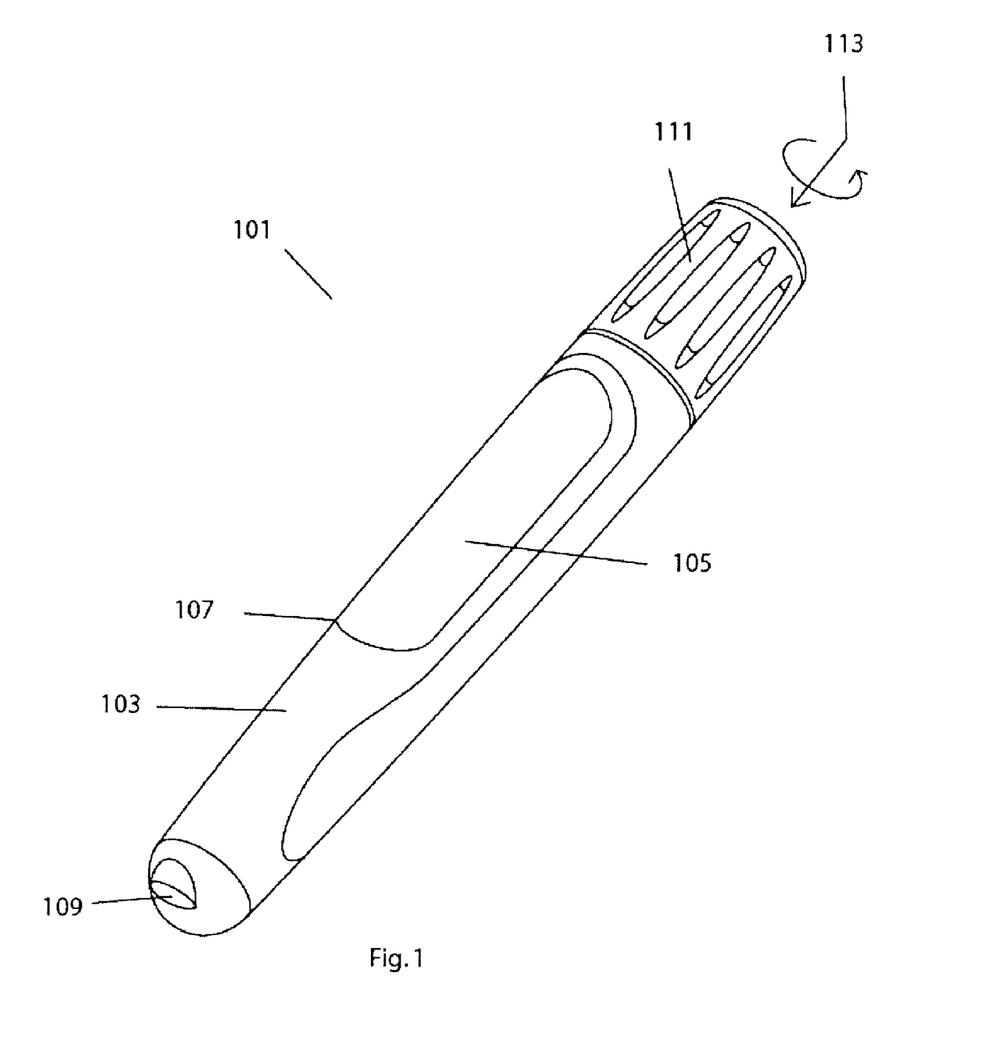
FIG. 1 is an isometric view of an analyte measurement device according to an embodiment of the present invention.

In accordance with an embodiment of the present invention and as illustrated in FIG. 1, an analyte measurement device 101 is provided for use with a test strip for determining the amount of an analyte in a sample. The device comprises:

(1) An analyte meter disposed within a housing 103. The analyte meter comprises: (i) a processor programmed to display a hierarchy of information or options having a plurality of levels to a user; (ii) a test strip interface for receiving a diagnostic test strip; and (iii) a meter display 105 communicatively coupled to the processor for displaying the hierarchy of information or options to a user. Each level of the plurality of levels comprises information selected from the group consisting of: a selectable lower level of information or options, a selectable upper level of information or options, a selectable subroutine performable by the processor, and a selectable parameter. A selectable subroutine performable by the processor is a diagnostic test subroutine where the processor is programmed to perform a diagnostic test on a sample applied to a test strip received within the test strip interface to determine a concentration of an analyte within the sample, and to store data in the hierarchy related to the test.

(2) A housing 103 having the analyte meter disposed therein and having a display opening 107 sized to receive the meter display 105 and make it visible to a user; and a test strip opening 109 sized to receive a test strip.

(3) A rotatable user interface 111, communicatively coupled to the processor and accessible on the outside of the housing 103, wherein the rotatable user interface 111 is rotationally and translationally connected about the housing 103 to permit rotation around an axis of rotation 113 and translation along the axis of rotation 113. When the rotatable user interface 111 is:
  (i) rotated around the axis of rotation 113, the meter display 105 scrolls through information or options in an open level, and
  (ii) translationally moved along the axis of rotation, a lower level of information is selected, an upper level of information is selected, a subroutine is selected, or a parameter is selected from the open level.

In a preferred embodiment the processor is programmed so that translational movement, rotational movement, or both translational movement and rotational movement of the rotatable user interface turns the meter from off to on. In a further preferred embodiment the test strip interface comprises a test strip detection electrode and the processor is programmed so that: when a test strip is inserted into the test strip interface the meter turns from off to on; when a test strip is removed from the test strip interface the meter turns from on to off; or both when a test strip is inserted into the test strip interface the meter turns from off to on and when a test strip is removed from the test strip interface the meter turns from on to off.

The present invention also provides a method for using the meter described above. The method of the present invention comprises the steps of, by the user,
  (i) rotating the rotatable user interface about the axis of rotation, and
  (ii) translating the rotatable user interface along the axis of rotation.

Where the processor is programmed so that translational movement, rotational movement, or both translational movement and rotational movement of the rotatable user interface turns the meter from off to on, the method further comprising the step of, by the user, turning the meter on by:
  rotating the rotatable user interface about the axis of rotation, moving the rotatable user interface along the axis of rotation, or both rotating the rotatable user interface about the axis of rotation, moving the rotatable user interface along the axis of rotation.

Where the test strip interface comprises a test strip detection electrode and wherein the processor is programmed so that: when a test strip is inserted into the test strip interface the meter turns from off to on; when a test strip is removed from the test strip interface the meter turns from on to off; or both when a test strip is inserted into the test strip interface the meter turns from off to on and when a test strip is removed from the test strip interface the meter turns from on to off, the method further comprising the steps of:
  by the user, turning the meter on, by inserting a test strip into the test strip interface the meter; and
  by the user, turning the meter off, by removing a test strip from the test strip interface.

Figure 2:
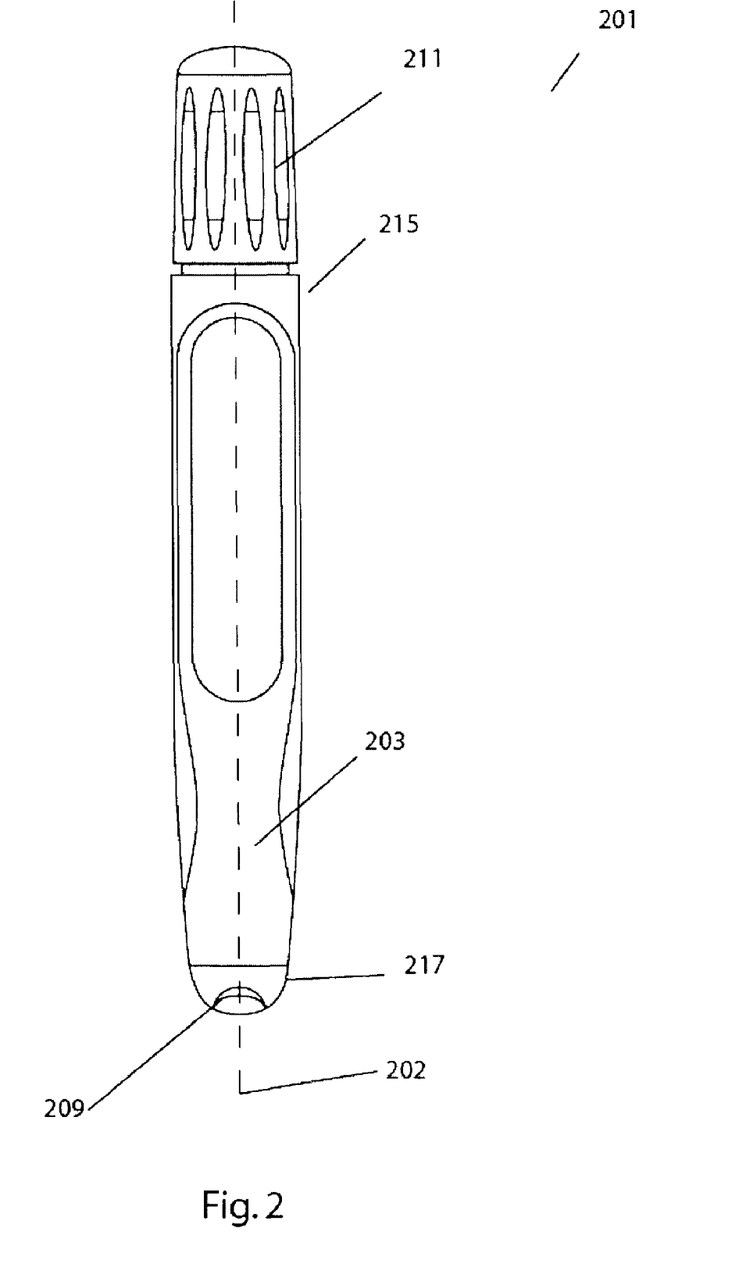
FIG. 2 is a front view of an analyte measurement device according to an embodiment of the present invention.

In another embodiment of the present invention, the analyte measurement device has an overall pen-shape. For example, as illustrated in FIG. 2, the housing 203 of the device 201 is generally annular and terminates at a first end 215 and at a second end 217 opposite the first end 215 of the housing 203. The generally annular housing 203 also has a central axis 202 extending through both the first 215 and second ends of the housing 203. The axis of rotation of the user interface is not limited and for example it may be at an oblique angle with respect to a central axis of the housing.

In FIG. 2, the rotatable user interface 211 is rotatably connected to the housing 203 at the first end 215 of the housing 203 and the test strip opening 209 is disposed at the second end 217 of the housing 203. The axis of rotation of the rotatable user interface 211 is along the central axis 202 of the housing 203.

Figure 3:
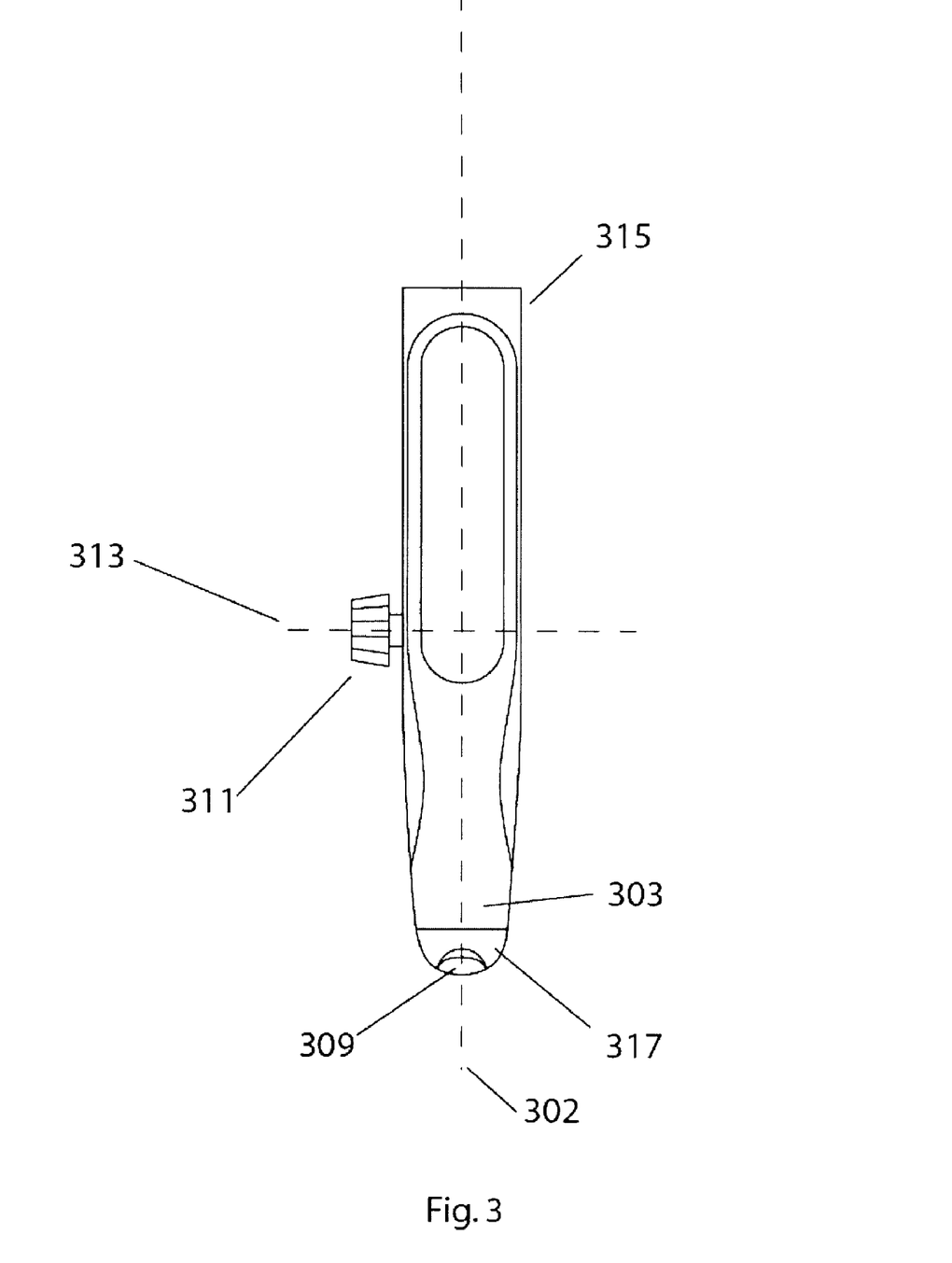
FIG. 3 is a front view of an analyte measurement device according to an embodiment of the present invention.

In another embodiment, as depicted in FIG. 3, the rotatable user interface 311 is rotatably connected to the housing 303 between the first 315 and second 317 ends of the housing 303 and the test strip opening 309 is disposed at the second end 317 of the housing 303. As shown in FIG. 3, the axis of rotation 313 of the rotatable user interface 311 is perpendicular to the central axis 302 of the housing 303.

The rotatable user interface may be rotated completely around the axis of rotation or it may be restrained from moving completely around the axis of rotation. In one embodiment the rotatable user interface is throttled so that as it is turned further away from an original position the information or options displayed on the screen is scrolled through at a faster pace.

The analyte meter is integrated into the housing and includes a display, a test strip interface, and a processor programmed to calculate and to store in the hierarchy of information the concentration of an analyte, preferably glucose, in a blood sample applied to a test strip received in the test strip interface. The housing has an opening for receiving the meter display as well as an opening for receiving a diagnostic test strip inserted into the test strip interface of the analyte monitoring meter. The analyte meter of the present invention is not limited and is preferably that described in US patent publication number US 2005/0265094, herein incorporated by reference.

Figure 4:
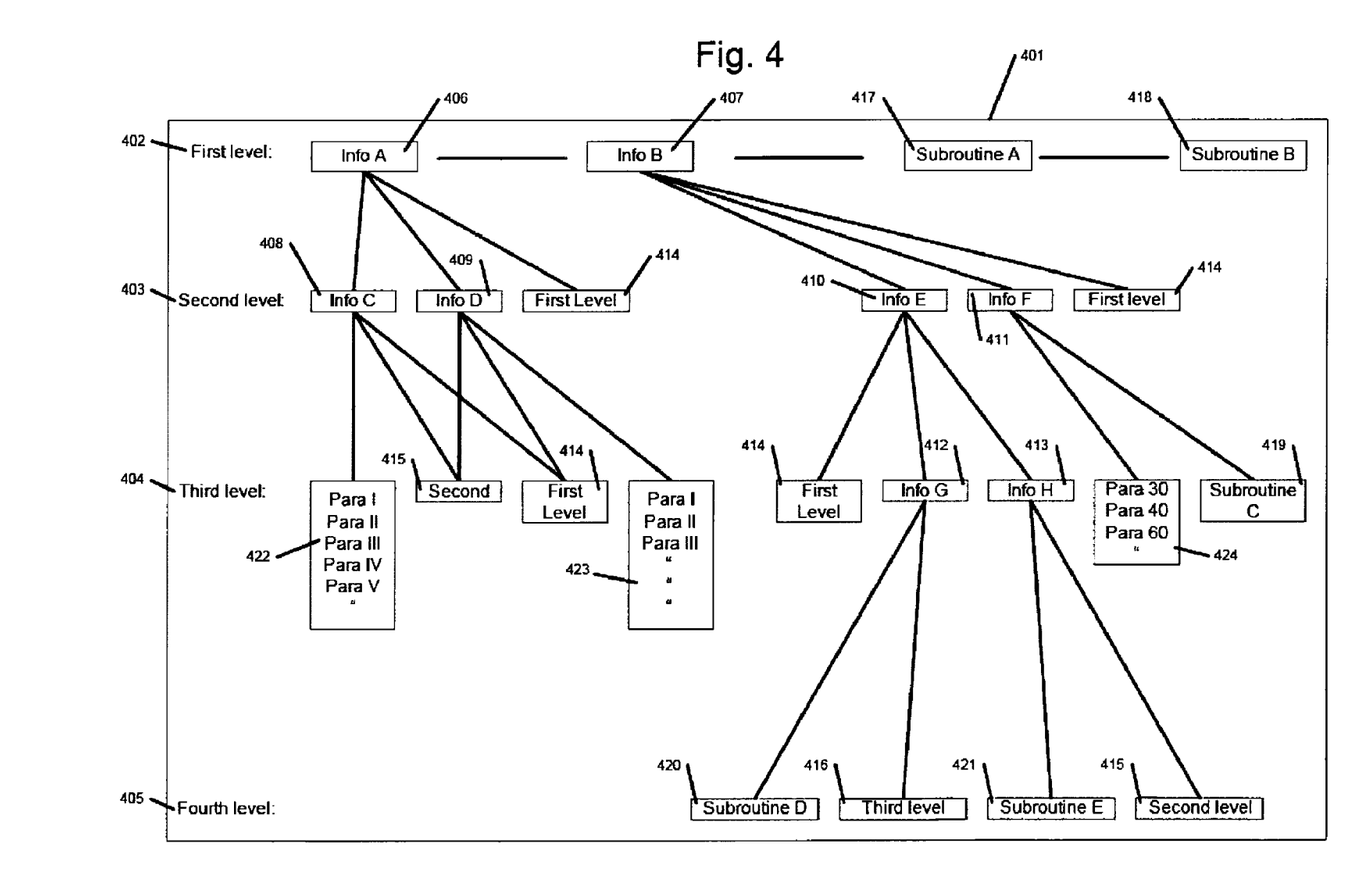
FIG. 4 is a schematic diagram illustrating an embodiment of the hierarchy of information of the device.

The processor of the meter is also programmed to display a hierarchy of information or options having a plurality of levels to a user. As shown in FIG. 4, each level (402, 403, 404, 405) of the plurality of levels of the hierarchy 401 comprises information or options selected from the group consisting of: a selectable lower level (406, 407, 408, 409, 410, 411, 412, 413), a selectable upper level (414, 415, 416), a selectable subroutine performable by the processor (417, 418, 420, 421), and a selectable parameter (422, 423, 424). As a user rotates the rotatable user interface around the axis of rotation, the display scrolls through selectable information or options contained in the open level. For example if the first level is open the user may scroll through selectable information or options comprising: Information A 406, Information B 407, Subroutine A 417, and Subroutine B 418. When a user translates the rotatable user interface along its axis of rotation one of the selectable information levels or options therein contained 406, 407, 417, 418 is selected.

Figure 5A:
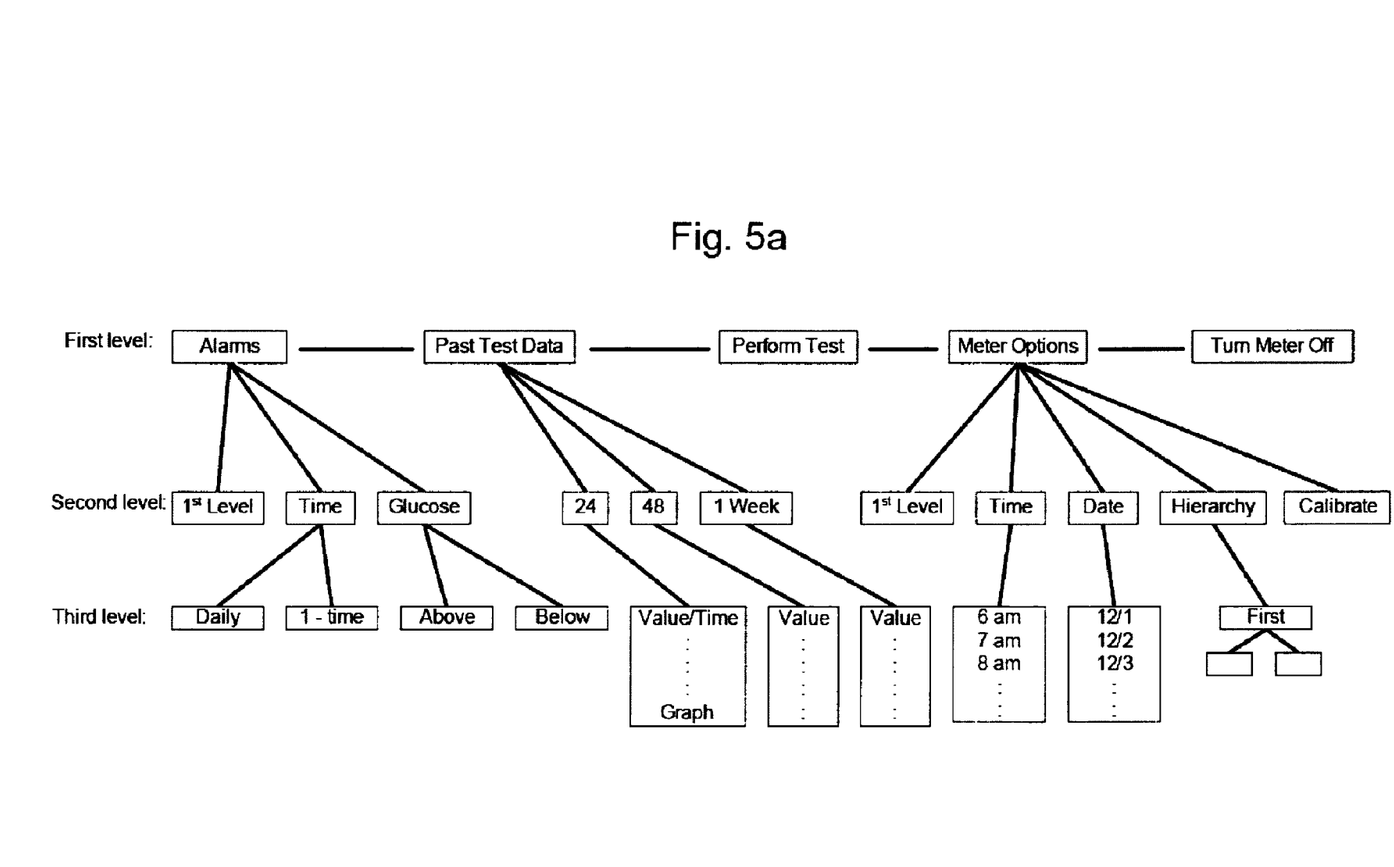
FIG. 5A is a schematic diagram illustrating an embodiment of the hierarchy of information of the device.

FIG. 5A illustrates an exemplary configuration of the hierarchy 501 of a meter in accordance with the present invention. In a first level, the hierarchy has selectable lower levels comprising selectable alarm options, selectable past test data, and selectable meter option information. The first level also has a selectable "perform-test" subroutine, and a selectable "turn-meter-off" subroutine. Each of these selectable lower levels and selectable subroutines options will be discussed below.

Selectable Alarm Information:

If a user selects this lower level from the first level in the hierarchy (i.e. by scrolling to the selectable alarm information option and translating the rotatable user interface along the axis of rotation) a second level of information or options is displayed. The second level comprises three options including an open a higher level option and two open lower level options. The open a higher level option, if selected, will open the first level. The two selectable lower levels comprise options for the user to set a time alarm or to set a measured glucose level alarm.

If a user selects the set a time alarm yet another lower level of selectable information or options will be displayed that comprises selectable parameters options for the user to select a time, or times, of the day that the alarm will sound. Such an alarm could be used to alert a user that a time has come for the user to test a sample.

If a user selects the set a glucose level alarm another lower level of selectable information or options will be display comprising selectable parameter options for the user to select a glucose level at which an alarm will sound if the level is exceeded in a subsequent diagnostic test. Such an alarm could be used to alert a user that the analyte measured in a sample has exceeded a preset value. For example, in the event that the analyte measured is glucose, the alarm could alert a user if a hypo/hyper glycemic level has been reached or if such a level is about to be reached.

Selectable Past Test Data Information:

If a user selects this option from the first level a second level of information or options appears on the display. In FIG. 5A, the second level comprises three options including an open a higher level option and three open lower level options. The open a higher level option, if selected, will open the first level as described above. The three lower levels comprise options for the user to select how the previous test data will be displayed (i.e. past 24 hours, past 48 hours, past week, and past month). Depending on what the user selects, the data will be displayed accordingly. An optional subroutine is provided in the test data under the past 24 hour results that illustrates that the processor may be programmed to display results in graphical format.

Selectable Meter Options Information:

If a user selects this option from the first level of information or options, a second level of information or options appears on the display. In FIG. 5A, the second level comprises various meter settings that a user is able to change, a meter calibration subroutine, and a go back to the first level option. Examples of changeable meter setting options are global date and time settings and optional hierarchy of information settings that allows a user to change what information is contained and displayed in the hierarchy.

Selectable "Perform-Test" Subroutine:

If a user selects this option from the first level, the processor will perform, and store data related to, a diagnostic test on a sample applied to a test strip received within the housing to determine the concentration of an analyte therein contained.

Selectable "Turn-Meter-Off" Subroutine:

If a user selects this option from the first level, the processor is programmed to and will shut the meter off.

Figure 5B:
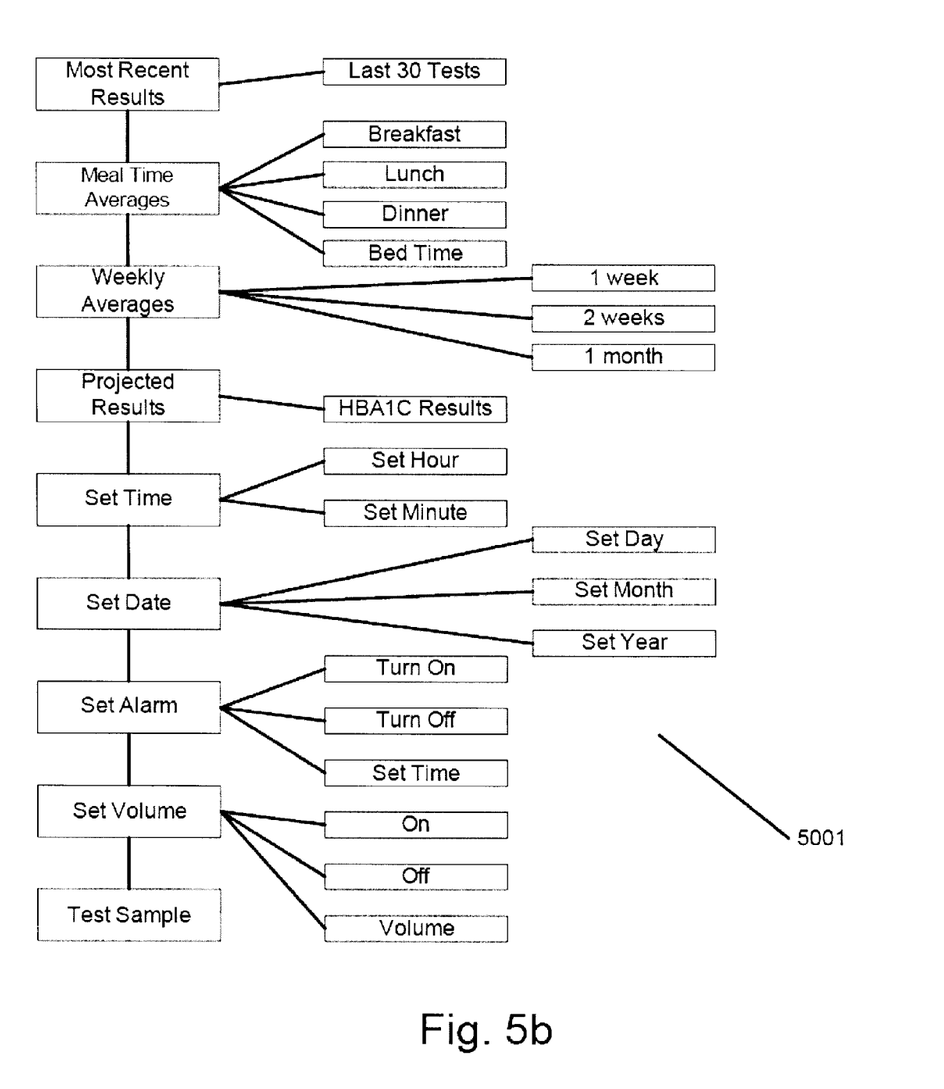
FIG. 5B is a schematic diagram illustrating an embodiment of the hierarchy of information of the device.

FIG. 5B illustrates yet another exemplary configuration of the hierarchy of information or options 5001 of a meter in accordance with the present invention. In a first level of information or options, the hierarchy has selectable lower levels of information or options comprising (1) a view the most recent test result selection, (2) a review meal time averages selection, (3) a review weekly averages selection, (4) a projected result selection, (5) a set time selection, (6) a set date selection, (7) a set an alarm selection, (8) a set the meter volume selection, and (9) a test a sample selection. As illustrated by the vertical lines in FIG. 5B, a user may scroll through the selectable lower levels of information (1) through (9), contained in the first level of information by rotating the user interface. After user selects one of the selectable lower levels of information or options the user may scroll through that level by again rotating the user interface.

One skilled in the art will appreciate that the examples provided herein of the hierarchy of information and options are only illustrative of a embodiments of the present invention. Numerous variations of the hierarchy including its contents and configuration are herein contemplated and do not depart from the scope of the present invention.

Figure 6:
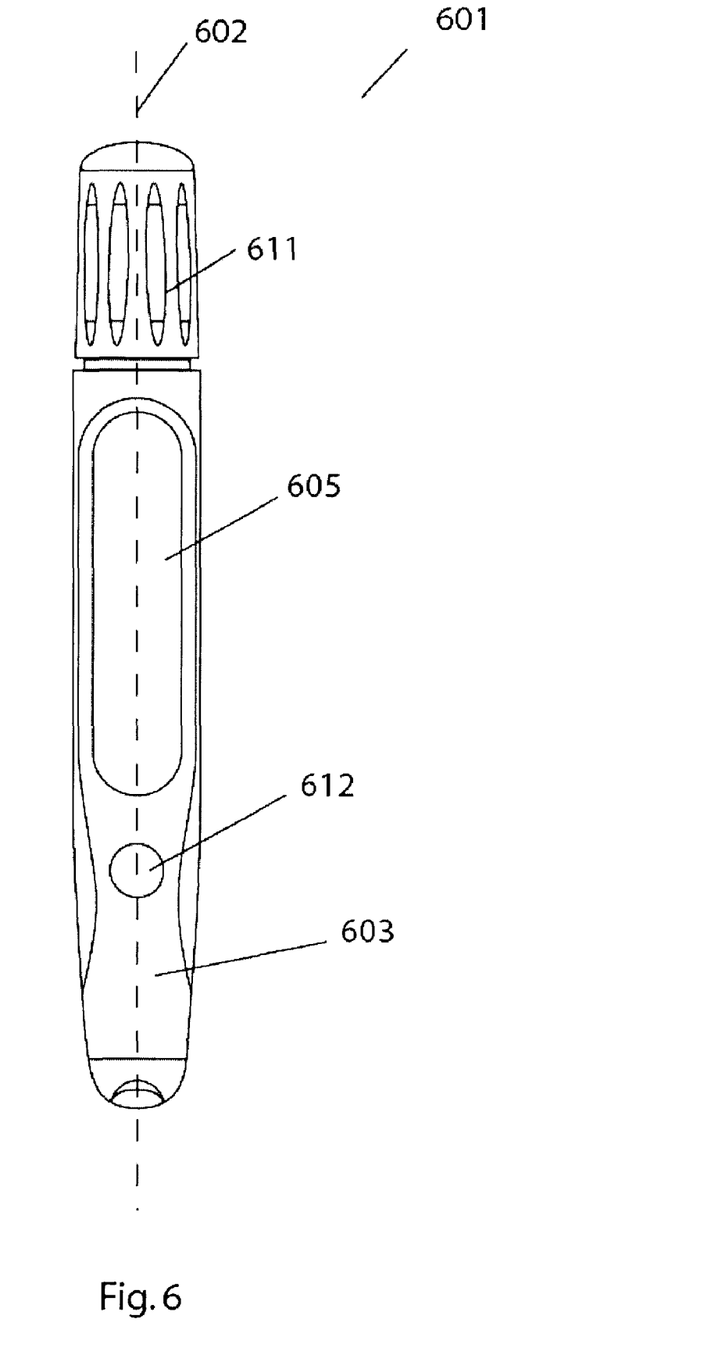
FIG. 6 is a front view of an analyte measurement device according to an embodiment of the present invention.

In another embodiment of the present invention an analyte measurement device is provided having a rotatable user interface and a selection user interface. In the present embodiment and as described in FIG. 6, the device 601 comprises:

(1) an analyte meter as described in any of the embodiments above, (2) a housing 601 as described in any of the embodiments above, (3) a rotatable user interface 611 communicatively coupled to the processor and accessible on the outside of the housing 603, wherein the rotatable user interface 611 is rotational around an axis of rotation 602, wherein when the rotatable user interface 611 is:

(i) rotated around the axis of rotation 611, the meter display 605 scrolls through information in an open level, and (4) a selecting user interface 612 communicatively coupled to the processor and accessible on the outside of the housing 603, wherein when the selecting user interface 602 is activated:

(i) a lower level is selected, an upper level is selected, a subroutine is selected, or a parameter is selected from the open level.

Figure 7:
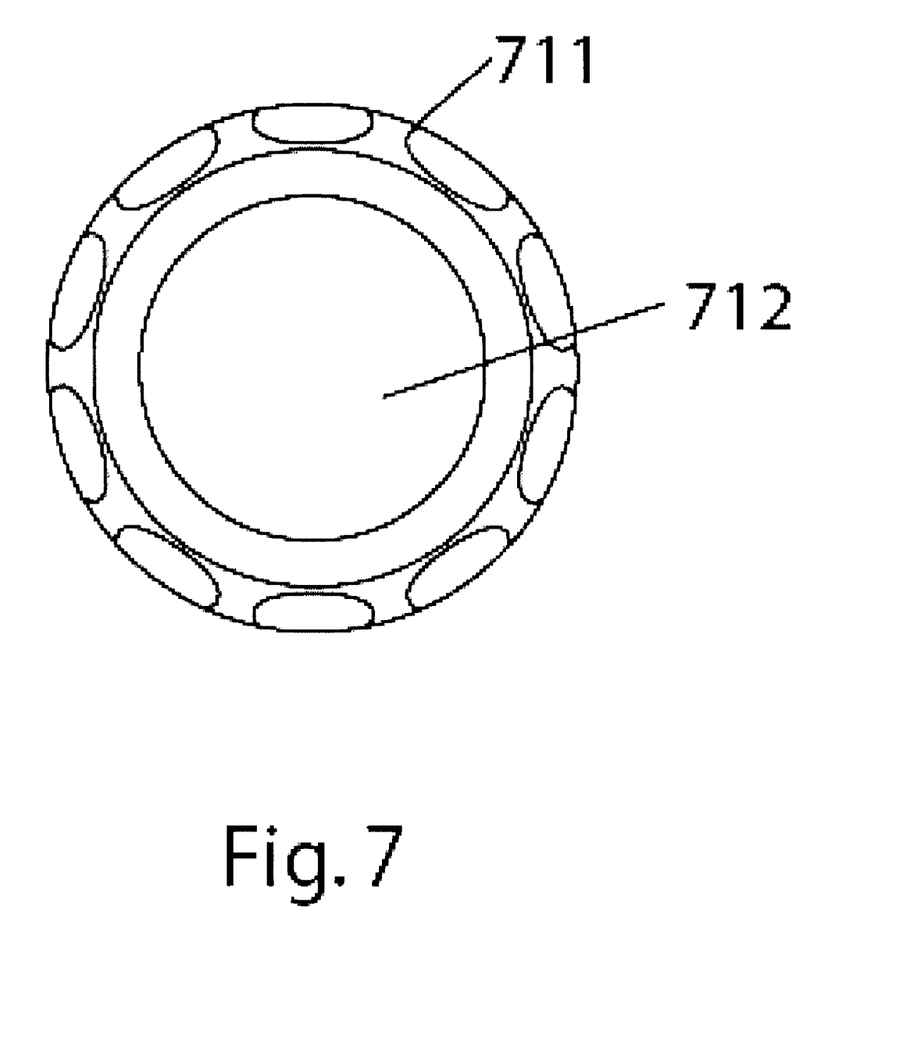
FIG. 7 is a top view of a rotatable user interface comprising a selecting user interface.
Figure 8:
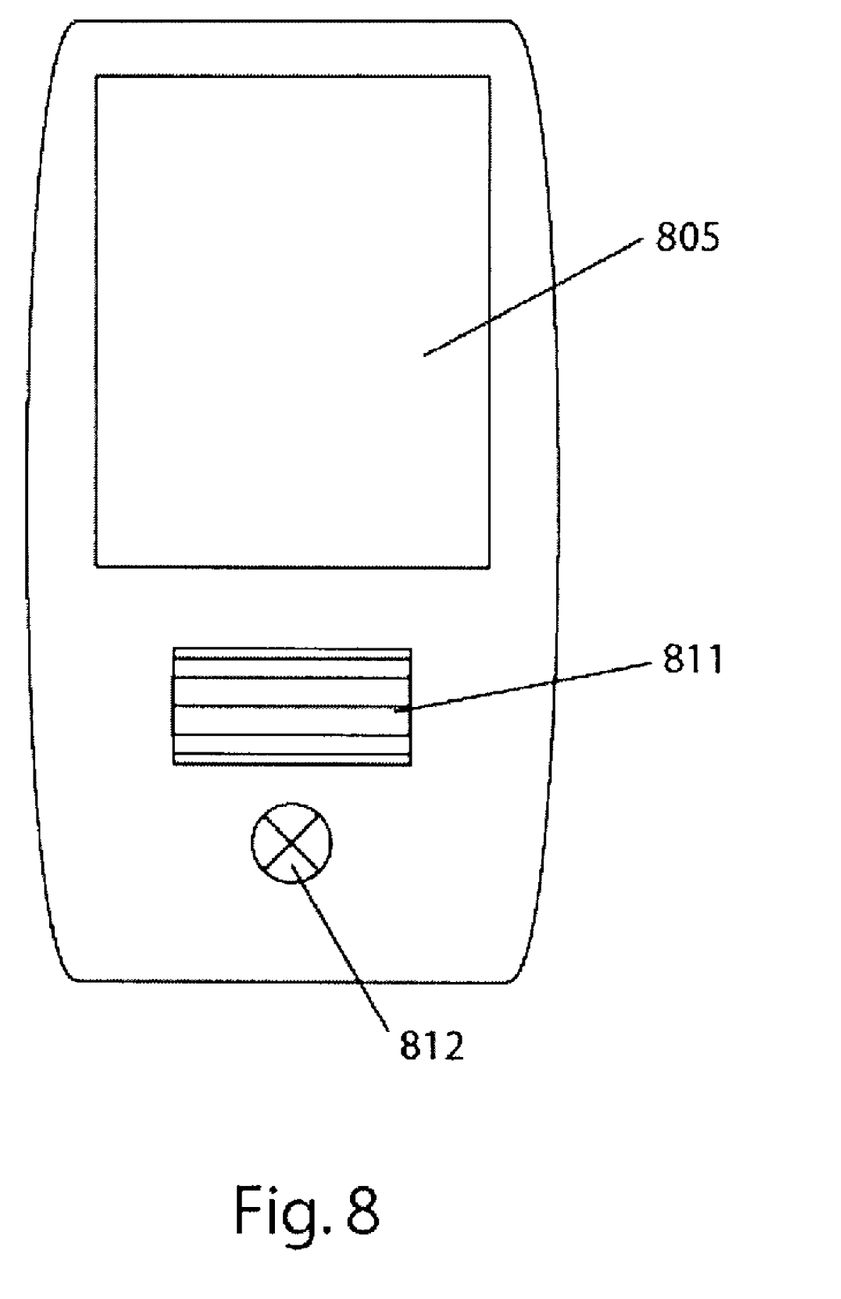
FIG. 8 is a front view of an analyte measurement device according to an embodiment of the present invention.

The selecting user interface may be a button, a knob, or another type of user interface that allows a user to select an individual piece of information from the hierarchy of information. Activation of the user interface may be by depression of, rotation of, or pulling on the selecting user interface. The selecting user interface and the rotatable user interface may be disposed anywhere on the device where the user has access to it. For example, as depicted in FIG. 7, the selecting user interface may be a button 712 on the rotatable user interface 711 located on an end of the housing. In another embodiment depicted in FIG. 8, the rotatable user interface is a wheel 811 displayed under the display 805 and the selecting user interface is a knob 812.

In the present embodiment the processor may be programmed so that activation of the selecting user interface, rotational movement of the rotatable user interface, or both activation of the selecting user interface and rotational movement of the rotatable user interface turns the meter from off to on.

Test strips suitable for use with the meter of the present invention are not particularly limited. As a non-limiting example, test strips that are suitable are disclosed in U.S. Ser. No. 10/908,656, which is herein incorporated by reference. Numerous test strips are also commercially sold. For example, test strips sold under the Accu-Check, One Touch Ultra, and Freestyle trademarks are suitable for use with the meters of the present invention.

The invention claimed is:

1. An analyte measurement device, for use with a test strip for determining the amount of an analyte in a sample, the device comprising:
   (1) an analyte meter comprising: (i) a processor programmed to display a hierarchy of information or options having a plurality of levels; (ii) a test strip interface for receiving a diagnostic test strip; and (iii) a meter display communicatively coupled to the processor for displaying the hierarchy of information or options to a user,
      wherein each level of the plurality of levels comprises information or options selected from the group consisting of: a selectable lower level, a selectable upper level, a selectable subroutine performable by the processor, and a selectable parameter, and
      one of the plurality of levels includes a selectable subroutine performable by the processor that is a diagnostic test subroutine where the processor is programmed to perform a diagnostic test on a sample applied to a test strip received within the test strip interface to determine a concentration of an analyte within the sample, and to store data in the hierarchy of information related to the test,
   (2) a housing having the meter disposed therein and having a display opening sized to receive the meter display and to make it externally visible to a user; and a test strip opening sized to receive a test strip, and
   (3) a rotatable user interface communicatively coupled to the processor and accessible on the outside of the housing, wherein the rotatable user interface is rotationally and translationally connected about the housing to permit rotation around an axis of rotation and translation along the axis of rotation, wherein when the rotatable user interface is:
      (i) rotated around the axis of rotation, the meter display scrolls through information or options in an open level, and
      (ii) translationally moved along the axis of rotation, a lower level of information is selected, an upper level of information is selected, a subroutine is selected, or a parameter is selected from an open level
   wherein a combination of rotation and translation of the rotatable user interface allows scrolling to and the selection of the diagnostic test subroutine.

2. The device of claim 1, wherein the hierarchy further comprises a turn-meter-off subroutine, where the processor is programmed to turn the meter off.

3. The device of claim 1, wherein a selectable lower level comprises alarm settings of the device.

4. The device of claim 3, wherein the alarm settings of the device comprise selectable alarm parameters related to tested analyte concentration and time.

5. The device of claim 1, wherein a selectable lower level comprises stored data from previous analyte tests performed by the processor.

6. The device of claim 5, wherein the stored data from previous tests performed by the processor is displayed to the user in increments selected from the group consisting of: past 1 day, past 2 day, past 7 day, and past month.

7. The device of claim 1, wherein the processor is programmed so that translational movement, rotational movement, or both translational movement and rotational movement of the rotatable user interface turns the meter from off to on.

8. The device of claim 1, wherein the test strip interface comprises a test strip detection electrode and wherein the processor is programmed so that: when a test strip is inserted into the test strip interface the meter turns from off to on; when a test strip is removed from the test strip interface the meter turns from on to off; or both when a test strip is inserted into the test strip interface the meter turns from off to on and when a test strip is removed from the test strip interface the meter turns from on to off.

9. The device of claim 1, wherein the housing is generally annular and has a central axis terminating at a first end and at a second end opposite the first end of the housing.

10. The device of claim 9, wherein the rotatable user interface is rotatably connected to the housing at the first end of the housing and the test strip opening is disposed at the second end of the housing.

11. The device of claim 10, wherein the axis of rotation of the rotatable user interface is along the central axis of the housing.

12. The device of claim 9, wherein the rotatable user interface is rotatably connected to the housing between the first and second ends of the housing and the test strip opening is disposed at the second end of the housing.

13. The device of claim 12, wherein the axis of rotation of the rotatable user interface is perpendicular to the central axis of the housing.

14. A method for use with an analyte measurement device for use with a diagnostic test strip for determining the amount of an analyte in a sample, the device comprising:
   (1) an analyte meter comprising: (i) a processor programmed to display a hierarchy of information or options having a plurality of levels to a user; (ii) a test strip interface for receiving a diagnostic test strip; and (iii) a meter display communicatively coupled to the processor for displaying the hierarchy of information or options to a user,
      wherein each level of the plurality of levels comprises information or options selected from the group consisting of: a selectable lower level of information, a selectable upper level of information, a selectable subroutine performable by the processor, and a selectable parameter, and
      one of the plurality of levels include a selectable subroutine performable by the processor that is a diagnostic test subroutine where the processor is programmed to perform a diagnostic test on a sample applied to a test strip received within the test strip interface to determine a concentration of an analyte within the sample, and to store data in the hierarchy of information related to the test, (2) a housing having the meter disposed therein and having a display opening sized to receive the meter display and to make it externally visible to a user; and a test strip opening sized to receive a test strip, and (3) a rotatable user interface communicatively coupled to the processor and accessible on the outside of the housing, wherein the rotatable user interface is rotationally and translationally connected about the housing to permit rotation around an axis of rotation and translation along the axis of rotation, wherein when the rotatable user interface is:
  (i) rotated around the axis of rotation, the meter display scrolls through information in an open level of information of the plurality of levels of information, and
  (ii) translationally moved along the axis of rotation, a lower level of information is selected, an upper level of information is selected, a subroutine is selected, or a parameter is selected from the open level of information, the method comprising the steps of, by the user,
  (i) rotating the rotatable user interface about the axis of rotation, and
  (ii) translating the rotatable user interface along the axis of rotation wherein a combination of rotation and translation of the rotatable user interface allows scrolling to and the selection of the diagnostic test subroutine.

15. The method of claim 14, wherein the processor is programmed so that translational movement, rotational movement, or both translational movement and rotational movement of the rotatable user interface turns the meter from off to on, the method further comprising the step of, by the user, turning the meter on by: rotating the rotatable user interface about the axis of rotation, moving the rotatable user interface along the axis of rotation, or both rotating the rotatable user interface about the axis of rotation, moving the rotatable user interface along the axis of rotation.

16. The method of claim 14, wherein the test strip interface comprises a test strip detection electrode and wherein the processor is programmed so that: when a test strip is inserted into the test strip interface the meter turns from off to on; when a test strip is removed from the test strip interface the meter turns from on to off; or both when a test strip is inserted into the test strip interface the meter turns from off to on and when a test strip is removed from the test strip interface the meter turns from on to off, the method further comprising the steps of: by the user, turning the meter on, by inserting a test strip into the test strip interface the meter; and by the user, turning the meter off, by removing a test strip from the test strip interface.

17. In an analyte measurement device having a housing and a processor programmed to display a hierarchy of information or options having a plurality of levels to a user and programmed to perform, and store data related to, a diagnostic test on a sample to determine a concentration of an analyte within the sample; the improvement comprising:

a rotatable user interface communicatively coupled to the processor and accessible on the outside of the housing, wherein the user interface is rotationally and translationally connected about the housing to permit rotation around an axis of rotation generally parallel to the central axis of the housing and translation along the axis of rotation, wherein when the rotatable user interface is:
  (i) rotated around the axis of rotation, the meter display scrolls through information in an open level of the plurality of levels of information or options, and
  (ii) translationally moved along the axis of rotation, a lower level is selected, an upper level is selected, a subroutine is selected, or a parameter is selected from the open level wherein a combination of rotation and translation of the rotatable user interface allows scrolling to and the selection of the diagnostic test subroutine.

18. An analyte measurement device, for use with a test strip for determining the amount of an analyte in a sample, the device comprising:

(1) an analyte meter comprising: (i) a processor programmed to display a hierarchy of information, or options having a plurality of levels; (ii) a test strip interface for receiving a diagnostic test strip; and (iii) a meter display communicatively coupled to the processor for displaying the hierarchy of information or options to a user,
  wherein each level of the plurality of levels comprises information or options selected from the group consisting of: a selectable lower level, a selectable upper level, a selectable subroutine performable by the processor, and a selectable parameter, and
  one of the plurality of levels includes a selectable subroutine performable by the processor that is a diagnostic test subroutine where the processor is programmed to perform a diagnostic test on a sample applied to a test strip received within the test strip interface to determine a concentration of an analyte within the sample, and to store data in the hierarchy of information related to the test, (2) a housing having the meter disposed therein and having a display opening sized to receive the meter display and to make it externally visible to a user; and a test strip opening sized to receive a test strip, and (3) a rotatable user interface communicatively coupled to the processor and accessible from the outside of the housing, wherein the rotatable user interface is rotational around an axis of rotation, wherein when the rotatable user interface is:
  (i) rotated around the axis of rotation, the meter display scrolls through information or options in an open level, and (4) a selecting user interface communicatively coupled to the processor and accessible on the outside of the housing, wherein when the selecting user interface is activated:
  (i) a lower level is selected, an upper level is selected, a subroutine, or a parameter is selected from the open level wherein a combination of rotation of the rotatable user interface and activation of the selecting user interface scrolls to and selects the diagnostic test subroutine.

19. The device of claim 18, wherein the hierarchy further comprises a turn-meter-off subroutine, where the processor is programmed to turn the meter off.

20. The device of claim 18, wherein a selectable lower level comprises alarm settings of the device.

21. The device of claim 20, wherein the alarm settings of the device comprise selectable alarm parameters related to tested analyte concentration and time.

22. The device of claim 18, wherein a selectable level comprises stored data from previous analyte tests performed by the processor.

23. The device of claim 22, wherein the stored data from previous tests performed by the processor is displayed to the user in increments selected from the group consisting of: past 1 day, past 2 day, past 7 day, and past month.

24. The device of claim 18, wherein the processor is programmed so that activation of the selecting user interface, rotational movement of the rotatable user interface, or both activation of the selecting user interface and rotational movement of the rotatable user interface turns the meter from off to on.

25. The device of claim 18, wherein the test strip interface comprises a test strip detection electrode and wherein the processor is programmed so that: when a test strip is inserted into the test strip interface the meter turns from off to on; when a test strip is removed from the test strip interface the meter turns from on to off; or both when a test strip is inserted into the test strip interface the meter turns from off to on and when a test strip is removed from the test strip interface the meter turns from on to off.

* * * * *